United States Patent [19]

Nomura et al.

[11] Patent Number: 5,055,103

[45] Date of Patent: Oct. 8, 1991

[54] DISPOSABLE GARMENTS

[75] Inventors: Hironori Nomura; Hirofumi Ohnishi, both of Iyomishima; Yoshinori Matsura, Kanonji; Tohru Sasaki, Kawanoe, all of Japan

[73] Assignee: Uni-Charm Corporation, Ehime, Japan

[21] Appl. No.: 626,783

[22] Filed: Dec. 13, 1990

[30] Foreign Application Priority Data

Dec. 18, 1989 [JP] Japan .................................. 1-328022

[51] Int. Cl.$^5$ .............................................. A61F 13/15
[52] U.S. Cl. .................................. 604/385.2; 604/358
[58] Field of Search .................. 604/385.1, 385.2, 386, 604/392, 358

[56] References Cited

U.S. PATENT DOCUMENTS 4,892,536 1/1990 DesMarais et al. ............... 604/385.2
4,895,568 1/1990 Enloe ................................ 604/385.2

Primary Examiner—Randall L. Green
Assistant Examiner—G. Gualtieri

[57] ABSTRACT

Here is disclosed an arrangement of elastic means surrounding respective leg-openings of garments such as disposable diaper, wherein the elastic means surrounding each of the leg-openings comprises a plurality of first elastic members and a plurality of second elastic members; the first elastic members are positioned substantially along a front half of the leg-opening while the second elastic members are positioned substantially along a rear half of the leg-opening; the first and second elastic members have their tensile stress gradually decreasing from their longitudinally inner ends toward their longitudinally outer ends; and the first and second elastic members have their inter-member spacings gradually enlarged from their longitudinally inner ends toward their longitudinally outer ends.

4 Claims, 2 Drawing Sheets

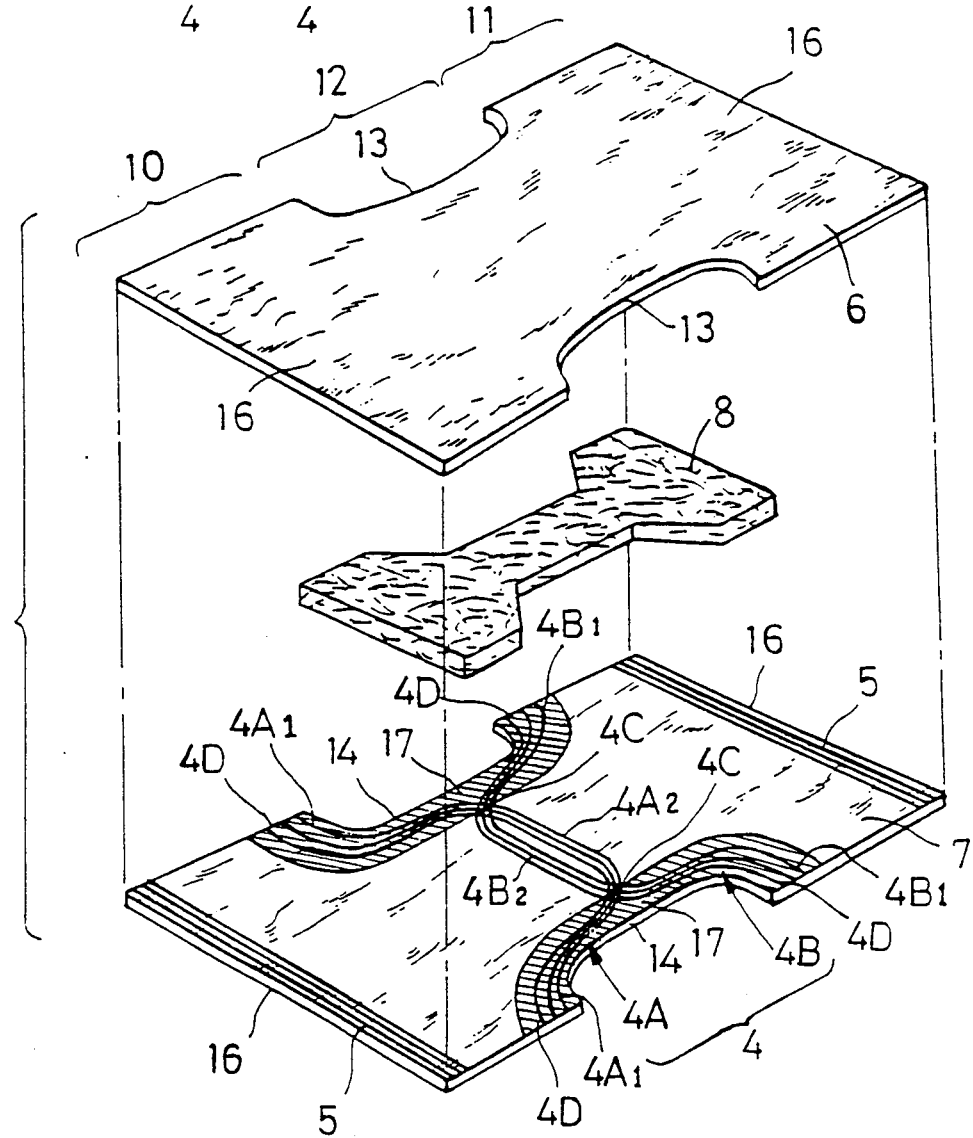

DISPOSABLE GARMENTS

BACKGROUND OF THE INVENTION

The present invention relates to disposable garments and more particularly to such garments such as diaper, incontinence pants and baby training pants.

The garments of such type are usually provided around the respective leg-openings with the elastic means. In general, the elastic means are bonded, under stretching, to at least one of the topsheet and the backsheet with adhesive.

With the particular garments, for example, a disposable diaper, undesirable leakage of excretions often occurs, regardless of the user's gender, at the opposite side of the crotch area defined between the opposite leg-openings due to location and orientation of the urinary organs.

Accordingly, it is preferred to provide an arrangement such that the elastic means have a higher tensile stress at the lower middle are of each leg-opening than at the remaining area and thereby allow the diaper to contact with the wearer's skin at this area with a higher fitness.

In view of a fact that, after put on the user, the diaper can move relative to the wearer's skin at the upper middle are of each leg-opening more easily than at said lower middle area, it is preferred also to decentralize the tensile stress of the elastic means at said upper middle area, allowing the diaper to contact with the wearer's skin over a relatively large area with a moderate fitness.

However, from the diaper having been proposed and commonly used in practice, no consideration can be found about gradually varying the tensile stress of the elastic means around the leg-openings and decentralizing the said tensile stress depending upon the area around the leg-openings.

It is a first object of the invention to provide the disposable garments including the elastic means surrounding each leg-opening which has a tensile stress gradually decreasing from adjacent the lower middle area toward adjacent the upper middle area of the leg-opening.

It is a second object of the invention to provide the disposable garments including the elastic means surrounding each leg-opening which has a tensile stress gradually decentralized from adjacent the lower middle area toward adjacent the upper middle area of the leg-opening.

SUMMARY OF THE INVENTION

The first object set forth above is achieved, in accordance with the invention, by disposable garments having a topsheet, a backsheet and elastic means provided around leg-openings defined at opposite sides of a crotch area connecting front and rear sections of the top- and backsheets, wherein the elastic means surrounding each of the leg-openings comprises first and second elastic members, the first elastic member is positioned substantially along a front half of the leg-opening while the second elastic member is positioned substantially along a rear half of the leg-opening so that the first and second elastic members intersect each other at their longitudinally inner ends located adjacent a lower middle of the leg-opening, and the first and second elastic members have their tensile stress gradually decreasing from the longitudinally inner ends toward their longitudinally outer ends.

The second object set forth above is achieved, according to the invention, by disposable garments as has been described above, wherein the elastic means surrounding each of the leg-openings comprises a plurality of first elastic members and a plurality of second elastic members and the first and second elastic members have their inter-member spacings gradually enlarged from their longitudinally inner ends toward their longitudinally outer ends.

In a preferred embodiment, the first and second elastic members surrounding each of the leg-openings are continuous to those surrounding the opposite leg-opening, respectively; and intermediate lengths of the respective continuous elastic members connecting the opposite leg-openings extend across the crotch area transversely thereof.

In this manner, the invention allows the garments to contact with the wearer's skin at adjacent the lower middle area of each leg-opening under a higher fitness than at the upper middle area thereof, since the first and second elastic members have the tensile stress gradually decreasing from their longitudinally inner ends toward their longitudinally outer ends, i.e., gradually increasing from their longitudinally outer ends toward their longitudinally inner ends.

Furthermore the tensile stress of the first and second elastic members is transversely decentralized in the proximity of the upper middle area of each leg-opening, since the first and second elastic members comprise a plurality of members, respectively, and their inter-member spacings are gradually enlarged from their longitudinally inner ends toward their longitudinally outer ends.

By using such garments of the invention, leakage of excretions readily occurring through the lower middle area of each leg-opening which has conventionally been remarkable and almost inevitable can be now effectively alleviated, since the invention allows the elastic members to contact with the wearer's skin in the proximity of the lower middle area of each leg-opening under a relatively firm fitness.

In addition, the upper area of each leg-opening most readily movable relative to the wearer's skin can be maintained in contact with the wearer's skin under a relatively weak tensile stress but over a large area, since the tensile stress of the elastic members is decentralized in the vicinity of the upper area of each leg-opening.

BRIEF DESCRIPTION OF THE DRAWINGS

FIG. 1 is a perspective view showing an embodiment of the garments constructed in accordance with the teaching of the invention;

FIG. 2 is an exploded perspective view of the garments; and

PREFERRED EMBODIMENT OF THE INVENTION

Figure 3:
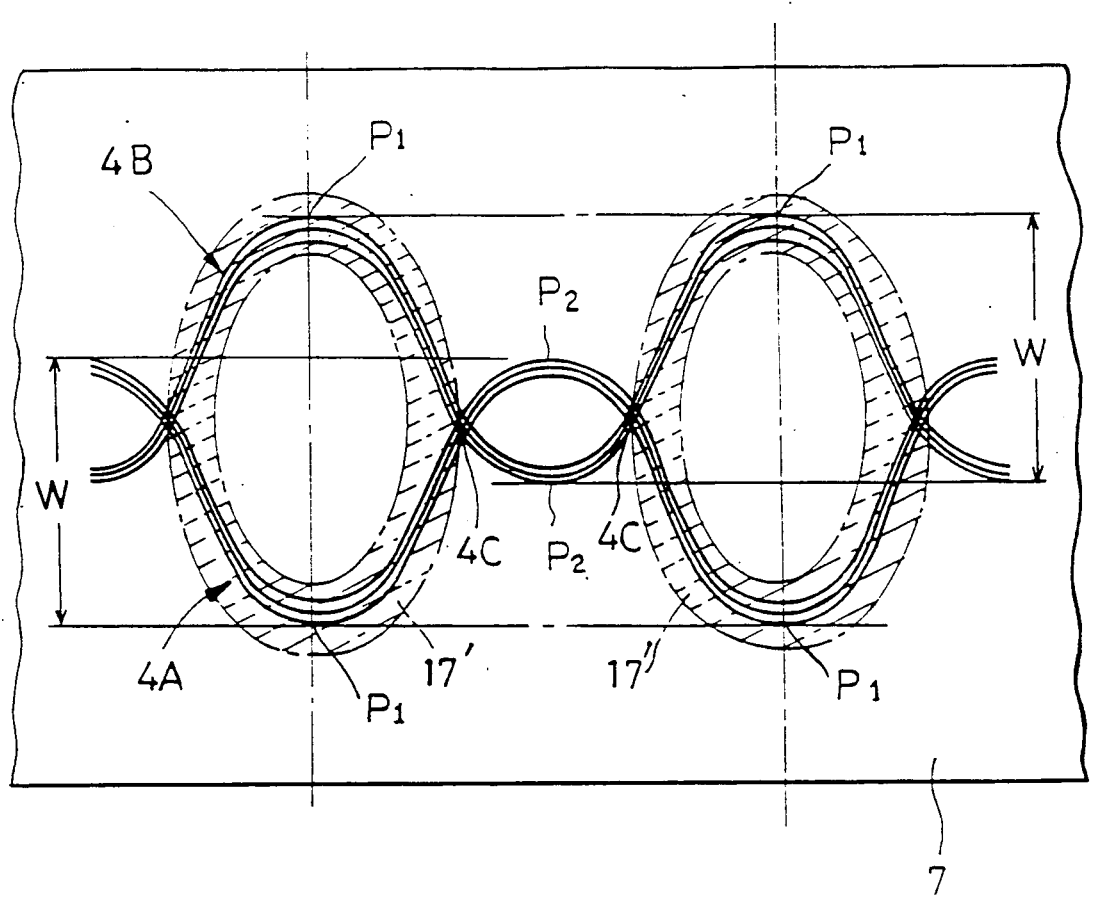
FIG. 3 is a plan view showing by way of example a manner in which elastic means is arranged.

The other features and advantages of the invention will be readily understood from the following description mad in reference with the accompanying drawings.

Referring first to FIG. 1, a diaper of pants type 1 is shown in a perspective view. As shown, the diaper 1 has leg-openings 2 and a waist-opening 3, both being provided with elastic means 4, 5, respectively.

Referring to FIG. 2, the same diaper 1 is shown in an exploded perspective view. As illustrated, the diaper 1 comprises a water-permeable topsheet 6 being stretchable both in length and width, a water-permeable backsheet 7 being also stretchable both in length and width, a mat- or sheet-like water-absorbent core 8, and the elastic means 4, 5 surrounding the leg-openings 2 and the waist-opening 3, respectively. Front and rear sections 10, 11 of the top- and backsheets 6, 7 define between the front and rear sections 10, 11 a crotch area 12 having opposite side edges formed with identical notched edges 13, 14, respectively, so as to define the respective leg-openings 2. The backsheet 7 may include water-impermeable plastic film (not shown) being stretchable both in length and width and bonded t the inner side of the backsheet 7 with adhesive intermittently applied thereto. Such arrangement will perfectly prevent excretions from passing through the backsheet 7. Where the film is bonded at least along its outer peripheral area to the topsheet 6 with intermittently placed spots of adhesive, the top- and backsheets 6, 7 as components of the diaper 1 will be improved not only in elasticity but also in tensile stress and thereby a fitness characteristic of the diaper 1 on the wearer's body will be further improved.

The elastic means 4 associated with the leg-openings comprises a plurality of first elastic members 4A and a plurality of second elastic members 4B. The first and second elastic members 4A, 4B extend in parallel to each other along their intermediate lengths $4A_2$, $4B_2$ and intersect each other substantially at middle points along the respective notched edges 13, 14, then extensions $4A_1$, $4B_1$ diverge from the respective intersections 4C so as to extend along the respective notched edges 13, 14. The divergent extensions $4A_1$, $4B_1$ are bonded to the inner surface(s) of the back- and/or topsheet(s) with adhesive 17 but the intermediate parallel lengths $4A_2$, $4B_2$ are positioned in substantially in a central area of the core across the crotch area 12 without being bonded to any of the back- and topsheets.

The first and second elastic members 4A, 4B are so arranged that the respective divergent extensions $4A_1$, $4B_1$ have the tensile stress gradually decreasing from their longitudinally inner ends (said respective intersections) 4C corresponding to bottoms of the respective leg-openings toward their longitudinally outer ends 4D corresponding to tops of the respective leg-openings, i.e., gradually increasing from their longitudinally outer ends 4D toward their longitudinally inner ends 4C.

In addition, a plurality of the first elastic members 4A and a plurality of the second elastic members 4B are so arranged to have their inter-member spacings along the respective divergent extensions $4A_1$, $4B_1$ gradually enlarged from their longitudinally inner ends 4C (said respective intersections) toward their longitudinally outer ends 4D, i.e. gradually reduced from their longitudinally outer ends 4D toward their longitudinally inner ends 4C (said respective intersections).

FIG. 3 is a plan view illustrating by way of example the manner in which the first and second elastic members 4A, 4B are arranged as has been described above. Adhesive is applied onto the backsheet 7 at given intervals longitudinally thereof so as to surround successive ellipses and thereby to define adhesive areas 17' while the backsheet 7 is moved longitudinally thereof at a given velocity. Simultaneously, a plurality of the first continuous elastic members 4A and a plurality of the second continuous elastic members 4B, both being stretched at a given elongation percentage, are inserted into the corresponding number of first and second traverses (not shown) which are, in turn, activated so that the first and second elastic members 4A, 4B are bonded to the backsheet 7 along the adhesive areas 17', describing curves substantially corresponding to sine curves. These curves are symmetric with respect to a longitudinally centre line of the backsheet 7. The first and second elastic members 4A, 4B travel from a starting point $P_1$ to a turning point $P_2$, then from the turning point $P_2$ to the new starting point $P_1$, respectively, by a width W for each cycle. Their elongation percentage increases during travel from the starting point $P_1$ to the turning point $P_2$ and consequently their tensile stress also increases, since the first and second elastic members 4A, 4B under stretching with a given elongation percentage having been linearly traveling longitudinally of the backsheet 7 are forcibly deflected by said traverses transversely of the backsheet 7, resisting against such deflection, and, in consequence, the first and second elastic members 4A, 4B are stretched in the course of traveling from the starting point $P_1$ to the turning point $P_2$, respectively. It will be understood that said elongation percentage depends upon the velocity at which the first and second elastic members 4A, 4B are fed longitudinally of the backsheet 7 as well as the velocity at which said traverses move transversely of the backsheet 7. Meanwhile, spacings of component elastic members in each plurality of elastic members 4A, 4B are reduced as each plurality of elastic members 4A, 4B having been linearly traveling longitudinally of the backsheet 7 is forcibly deflected by the associated traverse transversely of the backsheet 7 from the starting point $P_1$ to the turning point $P_2$. It will be understood here again that a degree of such inter-member spacing reduction depends upon the velocity at which the first and second elastic members 4A, 4B as well as the backsheet 7 travel.

The lengths (the intermediate parallel length $4A_2$, $4B_2$ in FIG. 2) of the first and second elastic members 4A, 4B extending between each pair of intersections 4C and being closely adjacent to each other are loosened to be brought further close together since the area of the backsheet 7 corresponding to these intermediate parallel lengths $4A_2$, $4B_2$ carries no adhesive. However, these intermediate parallel lengths also may be bonded to the backsheet 7 with adhesive, if desired, by applying adhesive onto said area of the backsheet 7 or the first and second elastic members 4A, 4B may be entirely coated with adhesive. In the latter case, obviously no adhesive will be applied onto the backsheet 7 a all.

The elastic means 5 surrounding the waist-opening is bonded to inner surface(s) of the top- and/or backsheet(s) with adhesive along a waist line 16.

Though not shown, the core 8 is bonded, on its top side and/or bottom side, to the topsheet 6 and/or the backsheet 7 with spots of adhesive intermittently placed thereon. A laminar structure formed in this manner may be folded in two along its longitudinally centre line and then opposite free edges thereof may be joined together by means of heat seal to provide the individual diaper 1 as shown by FIG. 1.

Such diaper 1 may be obtained by employing the method for making disposable briefs a disclosed in Japanese Patent Application No. 1989-167224 filed in the name of the same applicant as of the present application. However, it should be understood that the present invention is not limited to the form of pants or briefs.

Specifically, it is possible within the scope of the invention that, instead of folding said laminar structure along its longitudinally centre line in two followed by joining the opposite free edges together by means of heat seal, the rear section 11 of said laminar structure is provided at opposite sides with suitable fastener means such as strips of pressure tape by which the waist line 16 of the laminar structure (garments) is fixedly completed as in the case of so-called open type diaper. It is also possible even to omit the core 8, depending upon the type of garments.

The topsheet 6 and the backsheet 7 may be of water-permeable nonwoven fabric being stretchable both in length and width, the core 8 may be of fluffy pulp mixed with hightly water-absorbent polymer particles, and the elastic members may be of natural or synthetic rubber or the like.

What is claimed is:

1. Disposable garments having a topsheet, a backsheet and elastic means provided along leg-openings defined at opposite sides of a crotch area connecting front and rear sections of the top- and backsheets, characterized by that:

the elastic means surrounding each of the leg-openings comprises first and second elastic members;
   the first elastic member is positioned substantially along a front half of both leg-openings and traversing the approximate middle of the crotch area while the second elastic member is positioned substantially along a rear half of both leg-openings and traversing the approximate middle of the crotch area so that the first and second elastic members intersect each other the middle area of the crotch area of each leg-opening; and
   the first and second elastic members have their tensile stress gradually decreasing from locations adjacent the middle of each leg opening toward locations adjacent end of each leg opening.

2. Disposable garments having a topsheet, a backsheet and elastic means provided along leg-openings defined at opposite sides of a crotch area connecting front and rear sections of the top- and backsheets, characterized by that:

the elastic mean surrounding each of the leg-openings comprises a plurality of first elastic members and a plurality of second elastic members;
   the first elastic members are positioned substantially along a front half of each leg-opening and traversing the approximate middle of the crotch area while the second elastic members are positioned substantially along a rear half of each leg-opening and traversing the approximate middle of the crotch area so that the first and second elastic members intersect each other adjacent the middle area of the crotch area of each leg-opening; and
   the spacings between each of the first elastic members and between each of the second elastic members are gradually enlarged from their location adjacent the middle of each leg opening toward their ends.

3. Disposable garments as recited in claim 1, wherein the first and second elastic members respectively comprise plural elastic members and the spacings between each of the first elastic members and between each of the second elastic members are gradually enlarged from their location adjacent the middle of each leg opening toward their ends.

4. Disposable garments as recited in claim 2, wherein the first and second elastic members have their tensile stress gradually decreasing from their location adjacent the middle of each leg opening toward their ends.

* * * * *